US006465197B1

(12) United States Patent
Schatten et al.

(10) Patent No.: US 6,465,197 B1
(45) Date of Patent: *Oct. 15, 2002

(54) ASSAY FOR SPERM QUALITY

(75) Inventors: Gerald P. Schatten, Verona; Sara Steffen Zoran, McFarland; Calvin R. Simerly; Christopher S. Navara, both of Madison, all of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,580

(22) Filed: May 8, 2000

Related U.S. Application Data

(63) Continuation of application No. 08/481,859, filed on Jun. 7, 1995, now Pat. No. 6,103,481, which is a continuation-in-part of application No. 08/040,039, filed on Mar. 31, 1993, now abandoned.

(51) Int. Cl.[7] .......................... C12Q 1/02; G01N 33/53
(52) U.S. Cl. ...................... 435/7.21; 435/29; 435/960; 436/63; 436/906
(58) Field of Search ........................ 435/7.21, 29, 960; 436/63, 906

(56) References Cited

U.S. PATENT DOCUMENTS 5,200,398 A   4/1993  Strasberg et al.
5,219,729 A   6/1993  Hodgen
6,103,481 A * 8/2000  Schatten et al. ........... 435/7.21

OTHER PUBLICATIONS

Draber, P., et al., "Differences in the Exposure of C–and N–terminal Tubulin Domains in Cytoplasmic Microtubules Detected with Domain–Specific Monoclonal Antibodies," Abstract 110: 190089w, *Mammalian Biochem.*, 110: 495 (1989).
Holy, J., et al., "Spindle Pole Centrosomes of Sea Urchins Embryos Are Partially Composed of Material Recruited from Maternal Stores," *Dev. Biol.*, 147:343–353 (1991).
ICN Biomedicals, Inc., p. IB–3 (1993).
Le Guen, et al., "Microtubule and Centrosome Distribution During Sheep Fertilization," *Eur. J. Cell Biol.*, 48: 239–249 (1989).
Navara, C.S., et al., "Microtubule Organization in the Cow During Fertilization, Polyspermy, Parthenogenesis, and Nuclear Transfer: The Role of the Sperm Aster," *Dev. Biol.*, 162: 29–40 (1994).
Schatten, G., "The Centrosome and Its Mode of Inheritance: The Reduction of the Centrosomes during Gametogenesis and Its Restoration during Fertilization," *Dev. Biol.*, 165: 299–335 (1994).
Schatten, G., et al., "Acetylated α–Tubulin in Microtubules during Mouse Fertilization and Early Development," *Dev. Bil.*, 130: 74–86 (1988).

Schatten, G., et al., "Maternal Inheritance of Centrosomes in Mammals? Studies on Parthenogenesis and Polyspermy in Mice," *Proc. Natl. Acad. Sci. USA*, 88: 6785–6789 (1991).
Senn, A., et al., "Immunofluorescence Study of Actin, Acrosin, Dynein, Tubulin and Hyaluronidase and Their impact on In Vitro Fertilization," *Human Reproduct.*, 7: 841–849 (1992).
Sigma Immunochemicals, p. 89 (1993).
Simerly, C., et al., "The Paternal Inheritance of the Centrosome, the Cell's Microtubule–Organizing Center in Humans, and the Implications for Infertility," *Nature Medicine*, 1: 47–52 (1995).
Simerly, C., et al., "Microinjected Kinetochore Antibodies Interfere with Chromosome Movement in Meiotic and Mitotic Mouse Oocytes," *J. Cell Biol.*, 111L 1491–1504 (1990).
Sirard, M.A., et al., "The Culture of Bovine Oocytes to Obtain Developmentally Component Embryos," *Biol of Reproduct.*, 39: 546–552 (1988).
Stearns, T., News and Views Article for Simerly et al. Paper, *Nature Medicine*, 1: 1–3 (1994).
Yanagimachi, R., et al., "The Use of Zona–Free Animal Ova as a Test System of the Assessment of the Fertilized Capacity of Human Spermatozoa," *Biol. of Reproduct.*, 15: 471–476 (1993).
Zymed Laboratories, Inc., p. 49 (1993).
Navara, et al., "Individual Bulls Affect Sperm Aster Size and Quality: Relationship Between the Sperm and Centrosome and Development," *Molec. Biol of the Cell*, 4 (Suppl.) p. 142A, Abstract No: 828, (1993).
Calbiochem Immunochemicals, p. 424 (1993).
Chemical Abstracts, vol. 110, Draber, P., et al., "Differences in the Exposure of C–and N–terminal Tubulin Domains in Cytoplasmic Microtubules Detected with Domain–Specific Monoclonal Antibodies," Abstract 110: 190089w, *Mammalian Biochem.*, 110:495 (1989).

(List continued on next page.)

*Primary Examiner*—David Saunders
(74) *Attorney, Agent, or Firm*—Michael Best & Friedrich LLP; Teresa J. Welch

(57) ABSTRACT

A method for evaluating sperm quality is disclosed. The first step of the method is to obtain a quantity of sample mammalian sperm and a sample of mature mammalian oocytes. The oocytes are fertilized with the sperm and the cumulus cells are removed from the fertilized oocytes. The oocytes are then labelled with antibodies directed to microtubules and the labelled microtubules are observed microscopically. The microtubule pattern is evaluated for microtubule aster size and organization. In one preferred from of the present invention, the mammalian sperm and mammalian oocytes are of the same species. In another preferred form of the present invention, the mammalian sperm and oocytes are of different species.

11 Claims, 3 Drawing Sheets

OTHER PUBLICATIONS

Holy, J., et al., "Spindle Pole Centrosomes of Sea Urchin Embryos Are Partially Composed of Material Recruited from Maternal Stores," *Dev. Biol.* 147:343–353 (1991).

Simerly, C., et al., "The Paternal Inheritance of the Centrosome, the Cell's Microtubule–Organizing Center, in Humans, and the Implications for infertility," *Nature Medicine,* 1: 47–52 (1995).

Simerly, C., et al., "Microinjected Kinetochore Antibodies Interfere with Chromosome Movement in Meiotic and Mitotic Mouse Oocytes," *J. Cell Biol.,* 111:1491–1504 (1990).

Navara et al., Molec. Biol. of the Cell., 4, (Suppl), p. 142 A, Abstr. No. 828, 1993.*

* cited by examiner

Fertile Sub-fertile

Sperm Head

Centrin Staining

γ-Tubulin Staining

Aster Formation

ASSAY FOR SPERM QUALITY

CROSS REFERENCE TO RELATED APPLICATION

This application is a continuation of application Ser. No. 08/481,859 filed Jun. 7, 1995 U.S. Pat. No. 6,103,481, which is a continuation-in-part of application Ser. No. 08/040,039 filed Mar. 31, 1993 now abandoned.

STATEMENT REGARDING FEDERALLY-SPONSORED RESEARCH

This invention was made with United States Government support awarded by NIH Grant Nos. HD22902 and HD 12913. The United States Government has certain rights in this invention.

FIELD OF THE INVENTION

The present invention relates to methods for determining the reproductive quality of mammalian sperm. In particular, the present invention relates to determining reproductive quality by visualization of sperm characteristics related to the competence of sperm to initiate microtubule formation after fertilization.

BACKGROUND

Currently, there are a number of methods to assay or test for male fertility. Current tests test for sperm number, motility, and morphology, for the acrosome reaction, for the release of acrosin, and for the ability to penetrate into zona-free hamster oocytes, as well as the hemizona assay and assays for semen volume and anti-sperm antibodies. While many of these tests provide useful information, there are other mechanisms of sperm fertility failure not diagnosed by these tests, and no single test is a consistently accurate and reliable test of general sperm fertility. One of the more widely used tests, the penetration of sperm into zona-free hamster oocytes, has proven to be unreliable, providing significant percentages of both false positives (i.e. infertile men who pass the test) and false negatives (i.e. fertile men who fail the test). In addition, no present tests provide an indication of relative potency so as to indicate which sperm, e.g. from among potential donors, has greater fertilizing potential than other sperm.

Semen quality has been analyzed in a number of methods. The first parameter measured is simply volume of the ejaculate (Laboratory Manual for the Examination of Human Semen and Semen-Cervical Mucus Interaction Manual, World Health Organization, 1987). The semen is also screened for anti-sperm antibodies which interfere with fertilization. Anti-sperm antibodies are evaluated in several fashions such as by sperm agglutination, sperm immobilization and immunobead binding. The last example includes some commercially available tests such as SpermCheck (Bio-Rad, Hercules Calif.) and SpermMar (Ortho Diagnostic Systems; Beerse Belgium) and may be used for direct assay (binding to sperm) or for indirect assay (presence of sperm antibodies in the serum) (Khoo, et al., *Am. J. Reprod. Immunol.* 26:11–16, 1991).

Semen has also been screened for the presence of tumor associated trypsin inhibitor (TATI) (Barnti, et al., *Scand. J. Clin. Invest.* 51(Suppl. 207):51–53, 1991). Acrosin, an enzyme important during fertilization, is a serine protease with trypsin specificity. TATI has been shown to be present in semen and shown to be inhibitor of acrosin (Hoppe-Seylers, *Z. Physiol. Chem.* 365:819–825, 1984).

Sperm are also directly analyzed for a number of criteria. First, the sperm may be examined for normal morphology, total number of sperm, and number of viable sperm using a light microscope (Laboratory Manual for the Examination of Human Semen and Semen-Cervical Mucus Interaction Manual, World Health Organization, 1987).

Secondly, sperm may be examined for motility. Motility has been divided into two types: percentage of motile sperm vs. immotile sperm and percentage of motile sperm with forward progression vs. immotile sperm.

Two other tests of sperm activity are used, the sperm motility index, which is a measurement of disturbances in optical density of the semen (Bartoov, et al. *Fertil. Steril.* 56:108–112, 1991) and the resazurin reduction test, which measures reduction of the dye resazurin by a color change reaction (Glass, et al. *Fertil. Steril.* 56:743–746, 1991).

The integrity of sperm plasma membranes are evaluated using the hypo-osmotic swelling test (HOS-test In this test, sperm are evaluated for percentage showing swelling in hypo-osmotic media (Smith, et al., *Int. J. Androl.* 15:5–13, 1992). There is debate as to whether there is also significance in differential tail swelling patterns.

A popular test conducted to evaluate sperm quality is the hamster oocyte penetration test (HOP-test), sometimes referred to as the "humster" assay, first referenced above. Sperm are added to media containing zona free hamster oocytes. The hamster oocytes are then evaluated for penetration by the sperm and for decondensation of the sperm nucleus. This assay also analyzes the sperm's ability to capacitate and undergo the acrosome reaction, because these events are necessary for penetration (Yanagamachi, et al., *Biol. Reprod.* 15:471–476, 1976). While this test is sanctioned by the National Institutes of Health (NIH), and it is used commercially by the medical community, its predictive value is subject to question.

There are a number of industries which also evaluate sperm quality, for example, for the artificial insemination of domestic farm animals and other animals such as dogs, thoroughbreds, and llamas. In the case of domestic farm animals, the primary methods of evaluation are non-return rate, which is the percentage of bred animals (artificial insemination or natural breeding) which do not return into estrus, and the in vitro fertilization rate of homologous oocytes. In those animals which are naturally bred rather than artificially inseminated, the only evaluation is non-return rate. Therefore, there is a need in the art of reproductive biology for an assay that will evaluate the reproductive quality of a sperm sample.

There is also a need in the art for an assay that will evaluate the reproductive ability of sperm samples and identify and test for other modes of sperm reproductive failure.

SUMMARY OF THE INVENTION

The present invention describes several methods for assaying for sperm fertility and quality, all of which are based on tests for sperm capability to initiate microstructure formation in a fertilized oocyte or egg extract. The ability to test for microtubule formation initiation by sperm both allows for identification of a newly recognized form of sperm failure as well as an assay for relative sperm fertility.

Thus one aspect of the present invention is a method for evaluating relative sperm fertility. The first step of the method is to obtain a quantity of sample mammalian sperm and a sample of mature mammalian oocytes. The oocytes are fertilized with the sperm, and the cumulus cells are removed from the fertilized oocytes. The oocytes are then labelled with antibodies directed to microtubules, and the labelled microtubules are observed microscopically. The microtubule pattern is evaluated for microtubule aster size and organization emanating from the base of the sperm head.

In one preferred form of this aspect of the invention the mammalian sperm and the mammalian oocytes are of the same species. In another preferred form of the present invention the mammalian sperm and oocytes are of different species.

In another preferred form of the invention, the fertilized oocytes are labelled with anti-tubulin antibodies or antibodies to microtubule organizing antigens.

Another aspect of the present invention is a cell-free assay for sperm centrosome competence. This assay permits the convenient diagnosis of a form of sperm reproductive failure.

It is an object of the present invention to evaluate sperm samples for reproductive quality.

It is another object of the present invention to evaluate mammalian sperm to assay for causes of reproductive failure.

It is an advantage of the present invention that the reproductive quality of the sperm may be evaluated at the microtubule organizational level.

Other advantages, features, and objects of the present invention will become obvious after evaluation of the specification, drawings, and claims.

DESCRIPTION OF THE INVENTION

Figure 1:
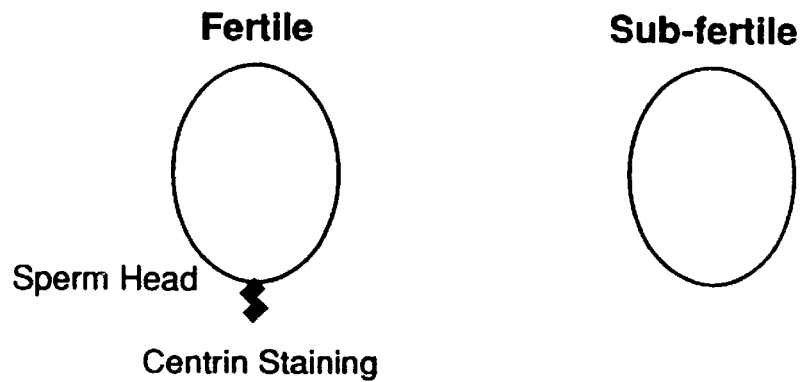
FIG. 1 is a diagram illustrating comparative microscope images of sperm tested in accordance with the present method.

The present invention is directed toward several methods for assaying the reproductive competence of mammalian sperm. For mammalian sperm to be effective during the fertilization process, it is well known that the sperm must be viable, must be capable of penetrating the oocyte, and must contribute a haploid set of chromosomes to the offspring. These contributions by the sperm are necessary, but are not sufficient for fertilization to occur. In addition, it is now clear that for most mammals, other than rodents, the sperm must donate the centrosome to the fertilized zygote. The centrosome then catalyzes the organization of microstructure proteins present in the oocyte, and thus initiates the formation of the microstructure in the fertilized oocyte, which ultimately results in the union of the paternal and maternal chromosomes into a fertilized zygote. Previously, there has been no generally available mechanism to evaluate the capability of a sperm to properly activate the cytoskeleton and biosynthetic machinery of the oocyte during fertilization. The methods described below are capable of testing for various aspects of that process of initiation of microstructure formation. These procedures are thus capable of clearly testing for a mechanism for a potential sperm reproductive failure heretofore elusive of efficient detection. In addition, as the results of the cellular assay described below will illuminate, these procedures can also be used to evaluate the relative reproductive fertility of sperm from various donors. It has been found that the competence of sperm cells to initiate and catalyze microtubule formation within the cells correlates well with the actual success rate of that sperm in achieving fertilization. In other words, a method is provided for judging the relative reproductive success rate of various lots of sperm, or of sperm from varying donors.

In general, it is now clear in humans that the father contributes the centrosome to the fertilized zygote. This fact appears to be true in almost all other mammals as well, with the notable exception of rodents. The oocyte contributes various other microstructural proteins which coalesce on a structure initiated by the sperm centrosome. While the paternal contribution of the centrosome has been suspected for some time, the inventors here, collaborating with others, have only recently demonstrated conclusively the paternal inheritance of the centrosome, Simerly et al., *Nature Medicine* 1:1:47–52 (1995). The significance of the mode of inheritance of the centrosome is also discussed in Schatten, *Developmental Biology* 165:299–335 (1994).

Based on this new understanding, and the development of tools capable of assaying for certain constituents of this process, it has now been possible to design clinical diagnostic procedures which can be utilized to assay for the competence of male sperm for the centrosomal contribution and its resulting cytoskeletal formation in the fertilized zygote. Several assays are described here.

One assay is to detect whether the paternally contributed essential centrosomal proteins are present on the human sperm. This is an in vitro test of sperm alone to visualize whether or not the necessary proteins are present on the sperm.

A second class of procedure is described below which assays the ability of the human mammalian sperm centrosome to attract the maternal components necessary for microstructure formulation. This second class of assay is conveniently performed using a cell-free extract from eggs. It is further described below that this assay can be conveniently performed with *Xenopus laevis* egg extracts, thus freeing the assay from the expense, difficulty, and limitations inherent in working with mammalian oocytes or even intact oocytes at all. This cell-free assay for sperm centrosome competence can thus be performed in an entirely cell-free manner, and provides results which correlate with the demonstrated ability of the sperm to achieve normal fertilization. A factor in the development of this assay is that the reduction of disulfide linkages in human sperm make that sperm capable of initiating microstructure formation in a Xenopus oocyte extract.

A third class of assay described below examines the ability of mammalian sperm to nucleate microtubules from the centrosome, after incubation in the cell-free extract, to provide a quick and reliable test of the competence of the human sperm to achieve this necessary part of the fertilization process.

Finally, a last test described herein tests the ability of mammalian sperm of varying degrees of fertility to nucleate microtubule formation in mammalian oocytes, including model test oocyte from cows, rabbits, sheep or pigs.

Thus a series of diagnostic tests is enabled which permit the testing of sperm from individuals, whether human or mammalian animal, of varying sperm motility and vigor to test for a necessary attribute of sperm which is heretofore not been capable of being tested. All four of the methods described below are quick, reproducible, and provide reliable results.

Applications of Tests

In General

This invention permits the rapid and non-invasive testing of mammalian sperm for centrosomal functions and competence, as well as for general level of fertility. Since centrosome function is essential to successful fertilization, these cell-free and cellular assays will help determine the fertilization potential of males.

Clinical: The present invention can be used for fertility testing of human males, both for suitability as natural fathers and as artificial insemination donors. Both for sperm donors and men needing fertility evaluation, these tests provide useful information about likelihood of reproductive success. For couples having fertility difficulties, these tests will help direct subsequent intervention strategies and, for example, suggest drug treatment or whether sperm or egg donors are required. In tests involving the evaluation of human sperm, it would be advantageous to use a test not utilizing cells, and a set of such tests are described below. For the cellular based test, as described below, test ova of a non-human nature, such as rabbit or bovine oocytes can be used.

Agricultural: The present invention can be used for selection of bulls, boars and other domestic species for artificial insemination. The method could be used for pretesting of male potency in vitro before natural matings. This test does not indicate the genetics of the offspring but does correlate with likelihood of reproductive success for the tested male.

Rare and Endangered Species: The present invention can be used for pretesting and selection of appropriate males before attempting natural and artificial insemination in rare and endangered species, such as elephants, large cats, and non-human primates.

Toxicology Evaluation: The present invention can be used to evaluate the effect of substances on the reproductive quality of sperm. Young male test animals will be treated with the potential toxic compound, and after sexual maturation, the effects of these compounds on the ability of the sperm to initiate fertilization and early development will be assessed during in vitro fertilization and embryo culture.

Contraceptive/Infertility Therapy Design: The present invention can be used to examine drugs which might either alter or enhance a sperm sample's ability to organize microtubules in oocytes. Analysis of drugs in this manner will have benefit for contraceptive or infertility treatment studies.

Identifying/Quantitating the Amount of Microtubule Organizing Factor: Another aspect of the present invention is identifying and quantitating the amount of microtubule organizing protein in sperm. For example, γ-tubulin can be examined to directly measure the ability to sperm to participate in microtubule organization without the need to test the effect after fertilization.

General Methods

Obtaining a Sperm Sample

Semen can be collected by whatever method is generally used for that species. For example, bull and rabbit semen is typically collected by use of an artificial vagina. Human semen is typically collected by manual ejaculation. Sperm should be washed via centrifugation and may be frozen prior to the assay, provided the freezing techniques do not destroy viability. The sperm sample may be diluted as appropriate.

Preparing Cell-free Oocyte Extracts

Cell-free extracts from oocytes can be prepared from any species for which oocytes can be obtained, but are routinely derived from frog oocytes. The oocytes are centrifuged, and the cytoplasmic fraction is separated. For non-mammalian oocyte extracts, reduction of disulfide linkages in the sperm will be useful in facilitating successful microtubule formation initiation in the extracts.

Obtaining Test Oocytes

For cellular tests, test oocytes may be of the same species as the sperm or may be of a different species. We expect a more pronounced reaction between sperm and oocytes of the same species, for example bovine oocytes and bovine sperm, but it is not always possible to obtain these oocytes. For example, in experiments with human sperm, one would wish to use test oocytes that are more easily obtained than human oocytes. We envision that the present invention will work between samples of different species.

Oocytes may be obtained surgically through standard procedures. After the immature oocytes have been obtained, they are matured by standard methods (Sirard, et al., *Biol. of Reprod.* 39:546–552 (1988)). If it is possible to obtain mature oocytes, these oocytes may be used and in vitro maturation is not necessary.

Fertilization and Labelling of Fertilized Oocytes

For the cellular tests, the test mammalian oocytes are fertilized with the sperm sample by standard in vitro methods. As described below in the examples, mature bovine oocytes are fertilized with bovine sperm in vitro and preferably cultured for approximately ten hours. Standard fertilization methods are not identical for each species. Those skilled in the art of reproductive biology know of appropriate techniques for each species.

After culturing, the cumulus cells are removed, preferably by incubation with 2 mg/ml hyaluronidase and manual stripping through a small bore glass pipette. The zona pellucidae are removed, preferably by a brief incubation in 2 mg/ml Pronase (Boerhinger Manheim). There are other methods known to those skilled in the art to remove cumulus cells and the zona pellucidae.

Fertilized oocytes are then recovered in maturation media in the incubator for 20 minutes after zona removal (See Sirard, et al., supra). Fertilized oocytes are then fixed, preferably by being attached to poly-l-lysine coated coverslips and fixed for 40 minutes with 2% formaldehyde in phosphate buffered saline (PBS) at 39° C. The formaldehyde is usually washed out with PBS containing 1% Triton X-100. Optimally, samples remain in this solution overnight.

The next morning, the coverslips are transferred to a petri dish containing 150 mM glycine in PBS to quench any remaining formaldehyde. After 10 minutes the coverslips are transferred to a petri dish containing 3% non-fat dry milk in PBS (Milk-PBS). This is done to block any non-specific labelling of the antibodies. Fertilized oocytes are then incubated with a monoclonal anti-tubulin antibody for 40 minutes in a humidified chamber. The examples below disclose the use of an antibody to β-tubulin. However, antibodies to other forms of tubulin, such as α-tubulin, are suitable for the present invention. As well as the source described below in the examples, anti-tubulin antibodies may be obtained from several commercial sources, for example Amersham and Sigma. After 40 minutes the coverslips are transferred back to a dish containing Milk-PBS for a 15 minute wash.

The location of the tubulin antibodies is then determined. Typically, samples are then labelled with a fluorescent secondary antibody specific for the first antibody. As above, this labelling is typically done in a humidified chamber for 40 minutes. After 40 minutes DAPI and propidium iodide are added to label the DNA in the sample. After ten minutes the coverslips are washed out with PBS containing 1%

Triton. The coverslips are mounted on glass slides in an antifade DABCO mounting media and examined on a microscope equipped for epifluorescence.

Evaluation of Sperm Constituents for Microtubule Formation (Cell-Free Assay)

The cell-free assays for the competence of sperm to initiate microtubule formation in the fertilization process begins with the visualization of the sperm to detect an assay for the presence of the paternally contributed molecules. This procedure does not require the cell-free assay, but is an immunological probing of the sperm themselves to detect the presence or absence of certain proteins or states which have been correlated with reproductive success. Fixed sperm are immobilized on coverslips for antibody staining. Then antibodies specific to the maternally donated protein centrin are probed against the immobilized sperm and visualized to detect the presence or absence of the centrin at the base of the sperm head. Similarly, phosphoproteins are localized at the sperm centrosome using a monoclonal antibody which has been developed against the generalized phosphorylated epitopes. Staining by this antibody indicates a phosphorylization status which has a negative correlation with male fertility. Fixing of the antibodies to the fixed sperm can be detected by microscopic fluorescence examination.

Figure 2:
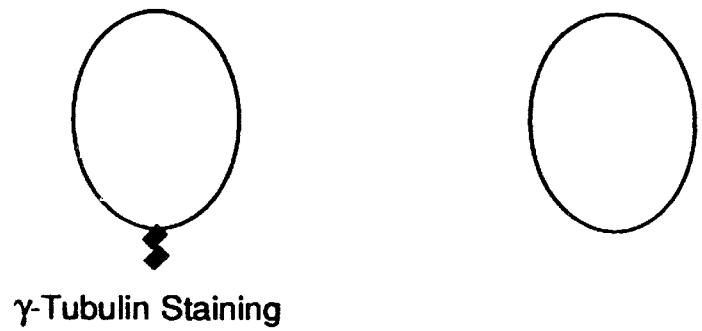
FIG. 2 is a diagram illustrating comparative microscope images of sperm tested under another aspect of the method.

To test for the competence of the sperm centrosomal constituents in attracting the maternal molecules necessary for microtubule formation, it is convenience to use the oocyte extract. Sperm is incubated with the oocyte extract and then processed for immunocytochemistry. For human sperm used with non-mammalian oocytes, such as the conveniently available Xenopus oocyte extract, the sperm must first be subjected to a disulfide reduction-step, which can be conveniently performed by dithiotreitol (DTT) incubation. The incubated mixture is then probed with antibodies specific to γ-tubulin and phosphorylated proteins. The γ-tubulin antibody binds to microstructurals formed in the mixture and permits their visualization again using fluorescently labeled antibody detection molecules and microscopy. Phosphoroproteins can be detected by immunological staining at the same time with antibodies specific to phosphorylated proteins. Indicated in FIG. 2 is a typical illustration of what can be viewed with the microscope, with the left-hand sperm in FIG. 2 indicating the presence of the γ-tubulin due to the proper staining at the base of the sperm head while the sub-fertile sperm at the right of FIG. 2 fails to show γ-tubulin presence.

Figure 3:
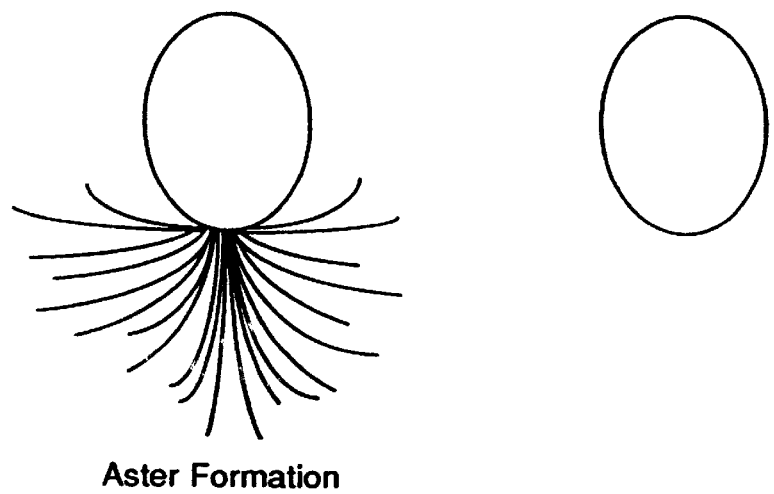
FIG. 3 is another diagram illustrating comparative microscope images resulting from another part of the present method.

It is then also possible to test for microtubule growth and nuclear decondensation in that same cell-free extract. After incubation with the extract containing fluorescently labelled tubulin, the forming aster in the extract is detected by incubations in the presence of a stain such as DAPI. Aster formation and size is then judged. As shown in FIG. 3, the normal sperm on the left shows correct and proper aster formation while the sub-fertile sperm on the right shows a failure to initiate aster formation using the maternally contributed molecules.

It has been found that for fertile males, a high proportion of the sperm from the fertile males will exhibit detectible centrin levels and will bind to the γ-tubulin specific antibodies. Very little of the sperm from fertile males will bind to the phosphorylation probe prior to incubation with the extract, while a significant portion of the sperm will bind to the phosphorylation antibody after incubation with the cell-free extract. For sub-fertile or infertile males, centrin will be present in a minority of the cells and will lack the ability to attract or bind γ-tubulin from the cell-free oocyte extract. By contrast, phosphorylation in sub-fertile males will be extensive even prior to incubation with a cell-free extract. Thus this cell-free extract provides a convenient and reliable mechanism for evaluating competence of human sperm to express paternally specific proteins, to attract maternally specific proteins, and to initiate microstructure formation in vitro.

Evaluation of Sperm Asters (Cellular Assay)

Figure 5:
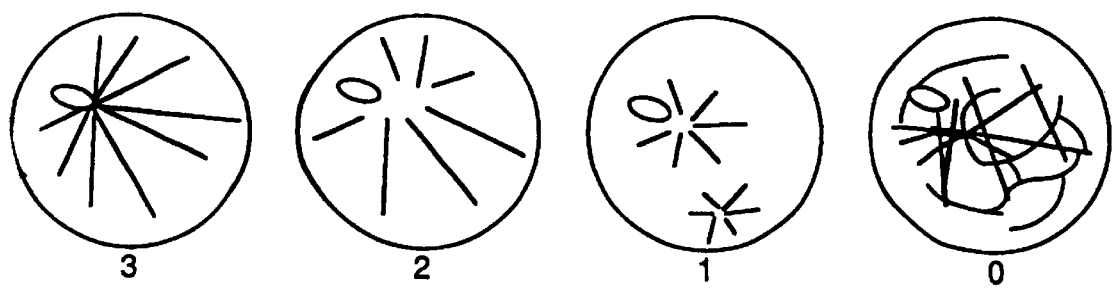
FIG. 5 is a diagram of four fertilized oocytes demonstrating the criteria for evaluating fertilized oocytes.

Sperm quality is measured by the presence, organization and size of a sperm aster (a microtubule array associated with the sperm nucleus). FIG. 5 depicts four different fertilized oocytes and the aster found in each. We have developed a classification system for these asters. As FIG. 5 depicts, a score of 3 indicates a large aster with a very tight focus. A score of 2 indicates a large aster with a more diffused focus. A score of 1 indicates a smaller aster with supernumary asters or disarrayed microtubule in the cytoplasm. A score of 0 indicates no apparent aster, although disarrayed microtubule are present. A score of 2 or above indicates a sperm sample that is adequate. Preferably, the score should be 2 or above. Preferably, an average of at least 10 fertilized oocytes should be evaluated.

The same scoring values might not be the same for all combinations of sperm and oocytes. In order to evaluate a system, one will typically experiment with the particular semen/oocyte combination before assigning numerical values. For example, one would take a sperm sample of known viability and test it in the system of the present invention. The value obtained by that sperm sample in a test oocyte would be assigned a high score. A sperm sample of known non-viability would be tested in the present system and assigned a low score. By this means, one could assign a value system to a specific sperm and oocyte combination.

Thus, high quality semen results in a larger, well-organized, sperm aster than low quality semen. Low quality sperm results in either no sperm aster, or in a very small aster forming with relatively few microtubule. Higher quality sperm also progress through the first cell cycle faster than lower quality sperm and a higher percentage of the subsequent embryos reach pre-implantation development.

Treatment of Sperm with Chemical Agents

Sperm samples are treated at increasing concentrations of chemical agents suspected of causing reproductive failure. These treated sperm samples are then analyzed for reproductive potential by the manner of the present invention. The results of assays are compared with results from untreated sperm from the same organisms using procedures described above, thus indicating the effect the chemical agent will have on the reproductive quality of a sperm sample.

EXAMPLES

I. Cellular (Oocyte Assay)

A. In General

The basic scheme of the present invention is to fertilize in vitro unfertilized mammalian oocytes with sperm of unknown quality. At about eight hours after insemination the fertilized oocytes are fixed and processed for immunocytochemical detection of microtubule and the fluorescence detection of DNA configurations. The length of microtubules, the normalcy of the microtubule-based structures (sperm aster, mitotic spindle meiotic spindle, midbody, cytasters and cortical arrays), and the speed of cell cycle progression are criteria employed to determine which sperm are likely to produce more offspring.

By "immature oocyte" we mean germinal vesicle stage oocytes which are recovered from post-mortem ovaries or by laparoscopy. "Mature oocytes" refers to oocytes which have been matured in vitro or in vivo and are arrested in metaphase of second meiosis.

B. Experimental Procedures

Bovine ovaries were obtained after slaughter and kept warm in normal saline. Immature oocytes were recovered from ovaries by aspiration of 5 mm follicles into a 10 ml syringe using an 18 gauge needle. The aspirate was expelled into a 45 ml plastic tube which was held in a water bath set at 39° C. The aspirate was examined using a Bausch and Lomb stereo microscope. Only those oocytes surrounded by several layers of cumulus cells and having a homogenous appearing cytoplasm were kept for maturation.

Oocytes which met this criteria were washed several times in Hepes buffered Tyrode's media (TL-HEPES) prepared according to Bavister, et al., (Biol. Reprod., 28:235, 1983) this was done to remove any inhibitory substances which may have been in the aspirate. The oocytes were then matured and fertilized in vitro as described previously. (Sirard, et al., Biol. Reprod., 39:546–552, 1988).

Cumulus cells were removed from the fertilized oocytes by passing through a small bore pipette (approximately 180 pm inner diameter) in the presence of 2 mg/ml hyaluronidase in TL-HEPES. After cumulus cell removal, the zona pellucidae of the oocytes were removed using a brief incubation (approximately 3 minutes) in 2 mg/ml pronase in protein-free TL-HEPES. The oocytes were put back into the incubator for a twenty minute recovery from the manipulations.

After twenty minutes of incubation the oocytes were attached to poly-l-lysine coated coverslips submerged in a petri dish containing Ca++, Mg++ free Phosphate Buffered Saline (PBS) at 39° C. PBS that contained 2% methanol-free Formaldehyde (also at 39° C.) was added until mixing was no longer detectable under the light microscope.

Oocytes were allowed to fix for 40 minutes in a 30° C. room. After 40 minutes the PBS+ Formaldehyde was replaced with PBS+ 1% Triton X-100 (PBS+Triton). Oocytes were left in PBS+Triton overnight. The next day the coverslips containing the oocytes were washed for 10 minutes with 150 mM Glycine in PBS. The coverslips were then washed for 10 minutes in PBS containing 3% non-fat dry milk (PBS+Milk).

After the 10 minute wash, the coverslips were placed in a humidified chamber and 100 μl of an anti-tubulin antibody was added. (We typically used E7, a commercially available mouse monoclonal antibody directed against β-tubulin [Developmental Hybridoma Bank, Iowa City Iowa]).

The humidified chambers were placed in a 39° C. dry incubator for 40 minutes. After this time, the coverslips were placed in petri dishes and washed for 15 minutes with PBS+Milk. The coverslips were again placed in humidified chambers and 100 μl of a fluorescein conjugated goat anti-mouse antibody, recognizing the first antibody, was added (Zymed).

Again, the chambers were placed in a 39° C. dry incubator for 40 minutes. After 40 minutes, 100 μl of a solution containing 2 mg/ml Propidium Iodide and 10 μg/ml DAPI was added to each coverslip, chambers were returned to the incubator for ten minutes. The coverslips were then washed for 20 minutes in PBS+Triton. The coverslips were then inverted onto glass slides in an antifade mounting media to prevent bleaching of the fluorescent label.

The coverslips were then examined on a ZEISS Axiophot microscope equipped with epifluorescence. Measurements were made on a Bio-Rad MRC-600 Laser Scanning Confocal Microscope. Microtubule asters were measured at plane of maximum diameter and recorded as a percentage of total cell volume.

C. Bovine Oocytes/Bovine Sperm

Bovine oocytes were fertilized with bovine sperm as described above. The fertilized oocytes were then processed as described and the size of the sperm asters evaluated at 11 hours post sperm addition. A qualitative score was assigned as follows: Asters were given a score of 3 if they had a single tight focus, a score of 2 if they had a single focus but the focus was more diffuse, a score of 1 was given if more than one focus was observed, and a score of 0 was given if no microtubule focus could be seen in the cytoplasm.

Figure 4:
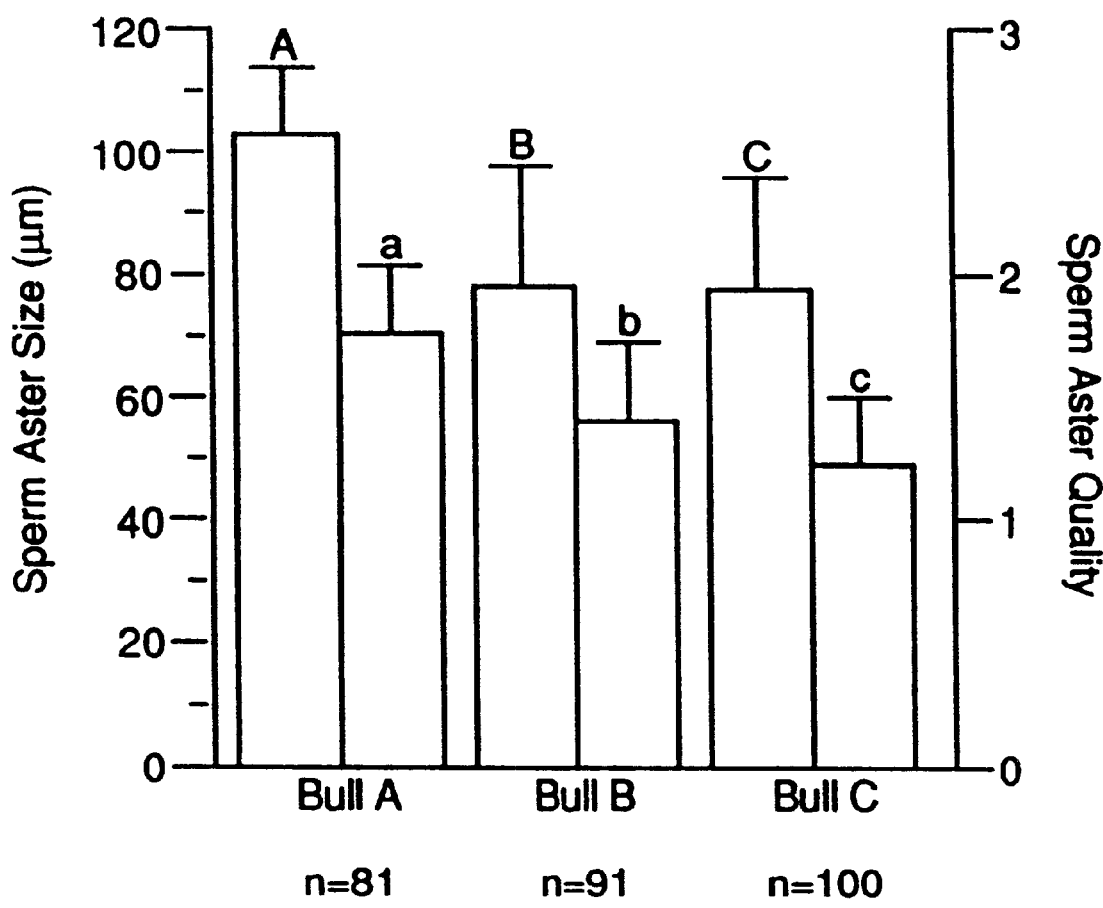
FIG. 4 is a diagram comparing bull reproductive quality and sperm aster size.

Three bulls having previously demonstrated fertility levels were evaluated; high in vivo and in vitro fertility (A), average in vivo and in vitro fertility (B) and poor in vitro fertility (C). The results from these experiments can be seen in FIG. 4. Multiple fertilizations with semen from Bull A resulted in a large mean aster size (85.38% of cell volume) with a single diffuse focus (average score=2.05). Fertilizations with semen from Bull B resulted in a much smaller mean aster (29.40% of cell volume) and some oocytes had supernumery asters in the cytoplasm (average score=1.50). Fertilizations with semen from Bull C resulted in a slightly larger mean aster than Bull B, but most oocytes contained supernumery asters or no aster at all (average score=1.08). This study validated the perceived association between microtubule formation and level of sperm fertility. This data is represented graphically in FIG. 4. The data was analyzed using the LSMeans method. The scoring difference between Bull A on the one hand, and Bulls B and C on the other hand, was statistically significant for sperm aster size. The scoring of sperm aster quality was statistically different for all three bulls and co-related to their actual demonstrated level of fertility.

The following Table 1 summarizes this data, with an indication of the level of sperm fertility, as indicated by development to morula stage of fertilized zygotes.

TABLE 1

|  | n | Non-Return to Estrus | Devel. to Morula | Sperm Aster Size (μm) | Sperm Aster Quality |
| --- | --- | --- | --- | --- | --- |
| Bull A | 81 | 79.5 | 36.0% | 101.4[a] | 1.8[a] |
| Bull B | 91 | 63.7 | 23.0% | 78.2[b] | 1.4[b] |
| Bull C | 100 | N.D. | 15.0% | 77.9[b] | 1.2[c] |

Different letters within a column indicate Statistical Difference ($p \leq 0.025$).

II. Cell-free Assays Paternally-Contributed Molecules in Sperm

1. Detection of Sperm Molecules

A. Preparation and Handling of Human Sperm: Human sperm were obtained from donors at IVF clinics or from sperm banks. Human donors were quality assessed by the World Health Organization (1987) standards for "normal" semen samples and the fertility records of these males were provided by sperm banks. All frozen sperm specimens were thawed for 10 minutes in a water bath at room temperature. Highly motile sperm were then selected by performing a buoyant density centrifugation step using a two-part Percoll gradient (2.0 ml of 45% Percoll and 2.0 ml 90% Percoll). The gradient was centrifuged at 700×g for 15 minutes, and the lowermost sperm layer rinsed in KMT medium (100 mM KCl, 2 mM $MgCl_2$, 10 mM Tris-HCl pH 7.0, 5 mM EGTA) by gentle centrifugation. Sperm were given a 10 minute treatment of 0.05% lysophosphatidylcholine in KMT which was followed by a 5 minute treatment of 3% bovine serum albumin (BSA) in KMT. For male pronuclear decondensation and centrosomal priming in vitro the sperm were incubated in 5 mM DTT for 60 minutes at 37° C., followed by 1 mM N-ethylmaleimide to irreversibly block thiol groups by alkylation, for 10 minutes at 200° C., and rinsed in KMT.

B. Immunocytochemical Detection of Centrin and Phosphorylated Epitopes in Human Sperm: Fixed sperm were blocked from nonspecific antibody staining by a 30 minute incubation in 0.1 M phosphate buffer saline (PBS: 137 mM NaCl/2.7 mM KCl/10 mM NaHPO$_4$/1.8 mM KH$_2$PO$_4$) containing 5% Normal Goat Serum (NGS); this solution, used for all rinses, was referred to as PBS-NGS. Centrin localization was performed using a mouse monoclonal antibody, 20H5, which was raised against bacterially derived *Chlamydomonas reinhardtii* centrin (Errabolu et al., *J. Cell Sci.* 107:9–16, (1994)). The Errabolu et al. paper describes how antibodies to this protein can be made. The fixed sperm were incubated with the primary antibody for 30 minutes at 20° C. at a dilution of 1:400. Phosphoproteins were localized at the sperm centrosome using a monoclonal antibody designated MPM-2 obtained from P. Rao, against general phosphorylated epitopes raised against mitotic HeLa cell extracts. Similar antibodies can be raised against mitotic extracts from this widely available cell line. The fixed sperm were incubated with the primary antibody for 30 minutes at 20° C. at a dilution of 1:300. After three rinses in PBS-NGS, the primary antibodies were detected using fluorescein-labelled goat anti-mouse antibodies diluted 1:40, and incubated for 30 minutes at room temperature. Controls for these experiments included staining the sperm with secondary antibody alone. DNA was fluorescently detected with 5 µg/ml DAPI (Sigma, St. Louis, Mo.)) added to the penultimate rinse. Coverslips were mounted in an antifade medium (Vectashield H-1000; Vector Laboratories, Burlingame, Calif.) to retard photobleaching.

C. Microscopy: Conventional fluorescence microscopy was performed using a Zeiss Axiophot microscope with high numerical aperture objectives. Black-and-white negatives were prepared with the Axiophot microscope using Tri-X film. Images were digitized using a Nikon Coolscan LS-10 (Melville, N.Y.) and were archived on an erasable magneto-optical disk. Digital data was downloaded to a dye-sublimation printer (Sony Corp. of America) using Adobe Photoshop software (Adobe Systems Inc., MountainView, Calif.).

D. Observation and Scoring: Sperm with positive staining at the centrosome (two dots at the base of the sperm head) were counted and percentages determined. These figure were compared between fertile and subfertile groups, as well as between controls in which no primary antibody was added to control for non-specific staining.

FIG. 1 illustrates the protypical results viewed. Sperm presenting the centrin molecule properly visualized as in the left-hand side of FIG. 1, while sperm from infertile males were as illustrated on the right-hand view. The data is summarized in Table 2 below.

2. Assaying maternal molecules attracted and bound to sperm after exposure to extract.

A. Sperm Preparation: Sperm were prepared as described in steps 1.A above.

B. Preparation of Xenopus Egg Extracts: Following methods of Stearns and Kirschner (1994), oocytes were induced to mature by injection of 100 I.U. PMSG into the dorsal lymph sac on day 1. A second injection of 500 I.U. hCG on day 4 induced the females to lay their eggs. Eggs, laid into MMR medium (10 mM NaCl, 2 mM KCl, 1 mM MgCl$_2$, 2 mM CaCl$_2$, 0.1 mM EDTA, 5 mM HEPES, pH 7.8), were collected 10–12 hours post-hCG injection. The eggs were dejellied by a 6 minute exposure to cysteine dejellying solution (100 mM KCl, 0.1 mM CaCl$_2$, 1 mM MgCl$_2$, 2% [w/v] L-cysteine, pH 7.8) and then rinsed four times in XB (Extract Buffer; 100 mM KCl 0.1 mM CaCl$_2$, 1 mM MgCl$_2$, 10 mM HEPES, pH 7.8, 50 mM sucrose, and 5 mM EGTA), and twice more in XB containing the protease inhibitors leupeptin, chymostatin, and pepstatin A (at 10 µg/ml each). The eggs were then transferred with a minimal volume of XB containing protease inhibitors and 100 µg/ml cytochalasin B into centrifuge tubes and overlaid with GE Versalube F-50 (Andpak-EMA). The eggs were packed during a two minute, 2000 rpm centrifugation in a SW50.1 rotor; the excess buffer and Versalube were removed. The eggs were then subjected to a stratifying centrifugation step of 20,000 rpm for 20 minutes in a SW50.1 rotor. The cytoplasmic layer was removed via a side puncture. This cytoplasmic extract was then fortified with an "Energy Mix" (150 mM creatine phosphate, 20 mM ATP, pH 7.4, 2 mM EGTA, pH 7.7, and 20 mM MgCl$_2$: 5 µl/100 µl extract) containing cytochalasin B and protease inhibitors (10 µg/ml each of leupeptin, chymostatin, and pepstatin A). For freezing, sucrose was added to the extract at a final concentration of 200 mM, and the aliquots were flash frozen in liquid nitrogen and stored at 70° C. 2 µg/ml nocodazole was added to the thawed extract just prior to incubation with sperm in all cases except where microtubule aster growth was desired.

C. Incubation of Sperm in Egg Extract: Human sperm were incubated with extract (approximately 1000 sperm/µl extract) and incubated at 37° C. for 60 minutes. Sperm were then rinsed with KMT. Coverslips were immersed in ice-cold methanol for 15 minutes and processed for immunocytochemistry.

D. Immunocytochemical Detection of γ-tubulin and phosphorylated epitopes in Human Sperm: γ-Tubulin localization was performed using a rabbit polyclonal antibody, XG-1-4, which is an affinity-purified antibody prepared against Xenopusγ-tubulin (Stearns and Kirschner, *Cell* 76:623–637 (1994); Stearns et al., *Cell* 65:825–836 (1991), each of which teaches how to make such antibodies). The fixed sperm were incubated with the primary antibody for 30 minutes at 20° C. at a dilution of 1:600. After three rinses in PBS-NGS, the primary antibody was detected using fluorescein-labelled goat anti-rabbit antibody diluted 1:40, and incubated for 30 minutes at room temperature. Phosphoproteins were localized with MPM-2 as described in I.B. After three rinses in PBS-NGS, the primary antibody was detected using fluorescein-labelled goat anti-mouse antibody diluted 1:40, and incubated for 30 minutes at room temperature. In all cases, DNA was fluorescently detected with 5 µg/ml DAPI (Sigma, St. Louis, Mo.)) added to the penultimate rinse. Coverslips were mounted in an antifade medium (Vectashield H-1000; Vector Laboratories, Burlingame, Calif.) to retard photobleaching.

E. Microscopy: Performed as in 1.C. above.

F. Observation and Scoring: Sperm with positive staining at the centrosome (two dots at the base of the sperm head) were counted and percentages determined. These figure are compared between fertile and subfertile groups as well as between controls in which no primary antibody was added to control for non-specific staining.

The typical results viewed are shown in FIG. 2. The left-hand sperm in FIG. 2 was from a fertile male while the right-hand sperm was from a sub-fertile male. The numerical results are set forth in Table 2 below.

3. Assaying microtubule growth and nuclear decondensation in cell-free egg extracts.

A. Preparation of Human Sperm: Sperm were processed as noted in section 1.A. with the following modifications. Human sperm were exposed to 5 μM ionomycin after the Percoll separation before receiving the additional treatments outlined in 1.A. However, all treatments were done in suspension.

B. Preparation of Xenopus Egg Extracts: Extracts were prepared as in 2.B. except that Nocodazole was deleted.

C. Incubation of Sperm in Egg Extract (Microtubule Assembly in Vitro Nucleated by Human Sperm): 1000 sperm in KMT were added to each μl of egg extract containing 0.08 mg/ml Xrhodamine-labeled tubulin prepared from porcine brains (gift from G. Borisy; the tubulin retains its capacity to assemble in vitro). Labelled tubulin is also commercially available from Cytoskeleton, Denver, Colo. The mixture was incubated for 60 minutes at 29° C. The nucleation and growth of the sperm asters were analyzed by mixing 1 μl of the extract/sperm/Rhodamine tubulin with 1 μl of PB containing 1 μg/ml DAPI and 0.5% Triton X-100. This preparation was mounted on a microscope slide, covered with a coverslip, and imaged with fluorescence microscopy using the rhodamine channel to directly detect microtubule assembly and the DAPI channel for DNA detection.

D. Observation and Scoring: Sperm with aster formation at the base of the sperm head were counted and percentages determined. These figures were compared between fertile and subfertile groups as well as between controls in which the sperm were not treated with DTT or in which no sperm were added to the egg extract.

The results of Examples II 1, 2, and 3 ar summarized in the following Table 2.

TABLE 2

|  | Fertile Men | Subfertile Men |
| --- | --- | --- |
| % Sperm with Centrin | 85% (23 males in 10 trials, 455 sperm) | 23% (1 male, 35 sperm) |
| % Sperm Which Attracted γ-Tubulin from Extract | 75% (24 males in 7 trials, 229 sperm) | 8% (1 male, 234 sperm) |
| % Phosphorylated Sperm (pre-Extract) | 11% (24 males in 7 trials, 310 sperm) | 90% (1 male, 32 sperm) |
| % Phosphorylated Sperm (post-Extract) | 65% (23 males in 6 trials, 132 sperm) | 100% (1 male, 30 sperm) |

4. Assaying sperm astral microtubule growth in a cellular system after insemination of homologous or heterologous oocytes.

1. Assay to be performed using heterologous species oocytes such as bovine, rabbit, guinea pig, pig A. Collection of Oocytes: Immature oocytes from bovine, porcine, and guinea pigs are collected and matured in vitro according to standard published protocols (bovine: Sirard et al., *Biol. of Reprod.* 39:546–552 (1988); pig: Kim et al, *Biol. of Reprod.* in press; guinea pig: Yanagimachi, R., *J. Reprod. Fert.* 38:485–488 (1974)). Mature ovulated metaphase-II arrested oocytes from hamsters and rabbits are collected from hormonally stimulated females according to published techniques (hamster: Bavister, *Gamete Res.* 23:139–158 (1989); rabbit: Yllera-Fernandez et al., *Mol. Reprod. Dev.* 32:271–276 (1992).

B. Insemination Technique: To determine if human sperm organize sperm asters in the mature oocytes of bovine, rabbit, guinea pig, porcine or hamsters, zona-free oocytes are prepared for insemination following the removal of the zona pellucidae with acid Tyrodes culture medium (pH 2.5), 0.5% trypsin or 0.5% pronase (reviewed by Simerly and Schatten, *Methods in Enzymol.* 225:516–553, 1993). After extensive rinsing in culture medium, human sperm collected from the swim-up protocol (Section I.A.) are diluted to a concentration of $1-5\times10^5$ sperm/ml and added to the zona-free oocytes for 3–10 hours of co-culture. After insemination, the zygotes are collected, washed free of unbound adhering spermatozoa, and processed for anti-tubulin immunocytochemistry. If normal insemination conditions do not provide adequate numbers of penetrated oocytes, then additional techniques are employed to induce heterologous sperm-oocyte fusion. Bovine oocytes that have been incubated with human sperm are subjected to an electrofusion pulse. Oocytes are removed from incubation with sperm after 3 hours, washed through three changes of culture medium, and then placed in Zimmerman Cell Fusion™ medium for a 1 min equilibration period. Oocytes are transferred to an electrofusion chamber and a 110V, 30 μs pulse is applied by a Zimmerman Cell Fusion instrument (Model Z1000, GCA/Precision Scientific Group, Ill.). After the electrofusion pulse, the oocytes are returned to culture.

C. Fixation Technique: Inseminated or electrofused zona-free oocytes from bovine, porcine, and guinea pig are attached to polylysine-coated coverslips and fixed in 2% formaldehyde (pH 7.4) for 40 min in 0.1 M PBS. Oocytes from hamsters and rabbits are first extracted in a microtubule stabilization buffer (Buffer M; composed of 25% (v/v) glycerol, 50 mM KCl 0.5 mM $MgCl_2$, 0.1 mM EDTA, 1 mM EGTA, 1 mM β-mercaptoethanol, and 50 mM imidazole-HCl at pH 6.8) with 1% Triton X-100 for 3 min before fixation in absolute methanol.

D. Immunocytochemistry: Formaldehyde fixed oocytes are permeabilized with 0.1 M PBS containing 1% Triton X-100 detergent overnight. Free aldehydes are reduced by a 30 min incubation in 0.1 M PBS with 150 mM glycine followed by a block in PBS+3% nonfat dry milk. Extracted oocytes are rinsed in 0.1 M phosphate-buffered saline with 0.1 Triton X-100 (PBS-TX). Microtubules are detected using monoclonal β-tubulin antibodies prepared against either glutaraldehyde-fixed microtubules (TU-27; 1:25, generously provided by Dr. L. Binder, University of Alabama, Birmingham, Ala.) or against bacterially expressed β-tubulin protein (E-7; cell line donated by the Developmental Studies Hybridoma Bank, Iowa, and grown here), applied for 1 hour at 37° C. Following a 20 minute rinse in PGS blocking solution, fluorescein- or rhodamine-conjugated goat anti-mouse IgG secondary antibody is applied for an additional hour at 37° C. to image the labeled microtubules. To detect centrosomes, rabbit γ-tubulin antibodies or mouse monoclonal anti-centrin antibody is applied to coverslips with adhering oocytes for 1 hour at 37° C. Unbound primary antibody is then removed by a 20 minute rinse in PBS blocking solution followed by the detection of centrosomes by incubation in fluorescein- or rhodamine-conjugated goat anti-rabbit IgG (γ-tubulin) or goat anti-mouse IgG (20H5) for 1 hour at 37° C. DNA is fluorescently detected with 5.0 μg/ml DAPI (Sigma) or propidium iodide (Molecular Probes) added to the penultimate wash. Cells are mounted in an antifade reagent (Vectashield; vectors Labs, Burlingame, Calif.) to retard photobleaching.

E. Observation and Scoring: Same as above.

We claim:

1. A method for assaying mammalian sperm in a sperm sample for reproductive competence comprising the steps of:

(a) exposing a portion of the sperm sample to disulfide bond reducing conditions;

(b) culturing the sample of step (a) with a cell-free oocyte extract under conditions favoring the formation of microtubule structures in the culture;

(c) visualizing the microtubule formation in the culture; and (d) checking for the existence of a sperm aster formation at the base of the sperm head as an assay of the reproductive competence of the sperm.

2. A method as claimed in claim 1 wherein the step (a) is performed by treatment with dithiothreitol.

3. A method as claimed in claim 1 wherein the step (b) is performed using extracts from Xenopus oocytes.

4. A method as claimed in claim 1 wherein the sperm is human sperm.

5. A method as claimed in claim 1 wherein the visualizing step is conducted by probing with antibodies for γ-tubulin and fluorescently labelling any binding antibodies.

6. A method for assaying human sperm in a sperm sample for reproductive competence comprising the steps of (a) exposing a portion of the sperm sample to disulfide bond reducing conditions;

(b) culturing the sperm sample of step (a) with a cell-free extract of Xenopus oocytes under conditions favoring the formation of microtubule structures in the culture;

(c) visualizing the microtubule formation in the culture; and (d) checking for the existence of a sperm aster formation at the base of the sperm head as an assay of the reproductive competence of the sperm in the sample.

7. A method as claimed in claim 6 wherein the step (a) is performed by treatment with dithiothreitol.

8. A method as claimed in claim 6 wherein the visualizing step (c) is performed using antibodies for γ-tubulin and fluorescently marking binding antibodies.

9. A method for evaluating the quality of sperm in a sperm sample comprising the steps of:

(a) combining mature mammalian oocytes containing microtubules with a portion of the sperm sample to yield fertilized oocytes;

(b) removing the cumulus cells from the fertilized oocytes;

(c) labeling the fertilized oocytes with antibodies directed to microtubules;

(d) visualizing the antibodies to detect microtubular structure; and (e) evaluating the microtubular structure of the fertilized oocyte for the presence, the size and the organization of a sperm aster to provide a score for sperm quality according to a predetermined scoring system, the score being an indicator of relative sperm quality, wherein the scoring system comprises a score range from 0 to 3, 0 being the score for no apparent aster present, 1 being the score for a smaller aster with supernumerary asters or more than one focus, or disarrayed microtubule in the cytoplasm, 2 being the score for a large aster with a diffuse focus, 3 being the score for a large single aster with a very tight focus.

10. A method for assaying mammalian sperm in a sperm sample for reproductive competence, comprising the steps of a) exposing a portion of the sample to disulfide bond reducing conditions;

b) incubating sample from step (a) with a cell-free oocyte extract containing a reagent for visualizing microtubules;

c) visualizing the microtubules; and d) determining the presence of a sperm aster formation at the base of the sperm head, the presence of the aster being an indicator of fertility.

11. The method of claim 10, wherein the oocytes of step (b) are Xenopus oocytes.

* * * * *